United States Patent

Pagan

[11] Patent Number: 6,021,779
[45] Date of Patent: Feb. 8, 2000

[54] LARYNGEAL MASK AIRWAYS AND THEIR MANUFACTURE

[75] Inventor: Eric Pagan, Hythe, United Kingdom

[73] Assignee: Smiths Industries Public Limited Company, London, United Kingdom

[21] Appl. No.: 09/006,821

[22] Filed: Jan. 14, 1998

[30] Foreign Application Priority Data

Feb. 5, 1997 [GB] United Kingdom .................. 9702337

[51] Int. Cl.$^7$ ........................ A61M 16/00; A61M 29/00
[52] U.S. Cl. ................................ 128/207.15; 128/207.14; 604/96
[58] Field of Search ........................ 128/207.15, 207.14, 128/200.26; 604/174, 96

[56] References Cited

U.S. PATENT DOCUMENTS 5,443,063  8/1995  Greenberg ........................... 128/207.15
5,881,726  3/1999  Neame ................................ 128/207.15

FOREIGN PATENT DOCUMENTS 2229367  9/1990  United Kingdom ............. 128/207.15

*Primary Examiner*—John G. Weiss
*Assistant Examiner*—Todd Martin
*Attorney, Agent, or Firm*—Pollock, Vande Sande & Amernick

[57] ABSTRACT

A laryngeal mask has a mount at its patient end of elliptical shape supporting an inflatable cuff. The cuff is a hollow extruded tube with an integral attachment flange and has opposite ends receiving two spigots on the mount. The attachment flange is attached to the mount by means of a projecting tooth, which locates in a channel around the mount.

9 Claims, 1 Drawing Sheet

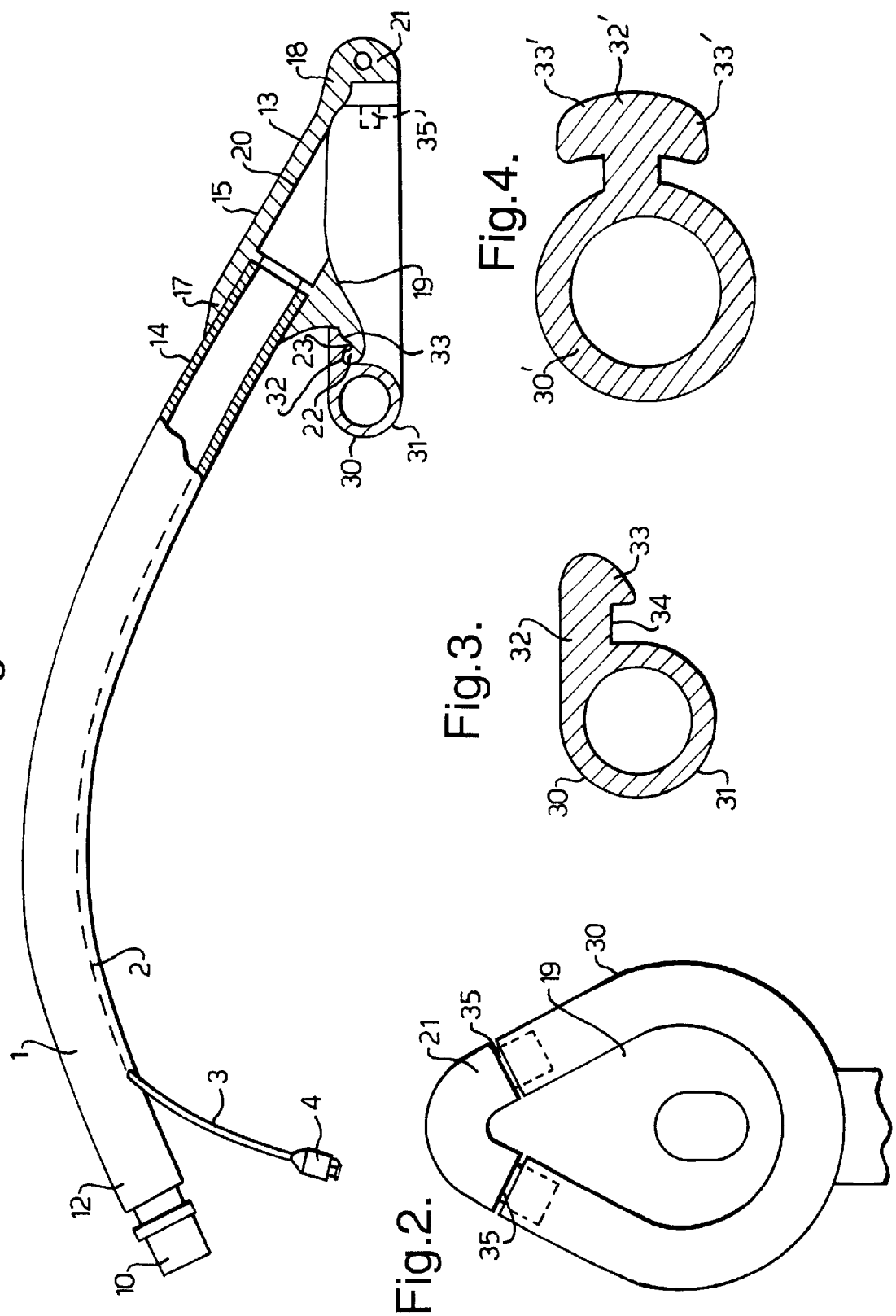

LARYNGEAL MASK AIRWAYS AND THEIR MANUFACTURE

BACKGROUND OF THE INVENTION

This invention relates to laryngeal mask airways and their manufacture.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2249959, GB 2111394, EP 448878, U.S. Pat. No. 4,995,388, GB 2205499, GB 2128561 and GB 2298797.

Laryngeal masks have several advantages over endotracheal tubes, which are longer and seal with the trachea below the vocal folds. It can be difficult, however, to manufacture the patient end of the mask at low cost.

SUMMARY OF THE INVENTION

It is an object of the present invention to provide an improved laryngeal mask assembly and improved method of manufacture.

According to one aspect of the present invention there is provided a laryngeal mask assembly comprising an elongate tube and a mask portion at the patient end of the tube, the mask portion including a mount member of generally elliptical shape having an opening therethrough communicating with the patient end of the tube and a hollow cylindrical cuff member extending around the mount member and attached with the mount member by an attachment flange projecting laterally of the cuff member along its length.

The mount member preferably has two spigots, opposite ends of the cuff member being open and mounted on respective ones of the spigots. At least one of the spigots preferably communicates with an inflation lumen extending along the tube so that the cuff member can be inflated via the lumen and each spigot. The attachment flange of the cuff member may have a projecting member extending along its length defining a channel between the projecting member and a tubular portion of the cuff member. The mount member may have a channel extending around its outer edge, the projecting member on the attachment flange being located in the channel on the mount member. Alternatively, the attachment flange may be of arrow shape cross section.

According to another aspect of the present invention there is provided a method of manufacture of a laryngeal mask assembly including the steps of providing an elongate tube having a mount member at its patient end, the mount member being of generally elliptical shape and having an opening therethrough communicating with the patient end of the tube, providing a hollow cylindrical cuff member having an attachment flange projecting laterally of the cuff member along its length, folding the cuff member about an outer edge of the mount member, and attaching the attachment flange to the mount member.

The cuff member is preferably extruded.

According to a further aspect of the present invention there is provided a laryngeal mask assembly made by a method according to the other aspect of the present invention.

A laryngeal mask airway assembly and its method of manufacture, according to the present invention, will now be described, by way of example, with reference to the accompanying drawings.

BRIEF DESCRIPTION OF THE DRAWINGS

FIG. 1 is a partly-sectional side elevation view of the assembly;

FIG. 2 is an underside view of the patient end of the assembly;

FIG. 3 is a transverse cross-side view, to an enlarged scale, of the cuff; and

FIG. 4 is a transverse cross-side view, to an enlarged scale, of an alternative cuff.

DETAILED DESCRIPTION OF THE PREFERRED EMBODIMENTS

With reference to FIGS. 1 to 3, the assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 communicates with the mask portion 13.

The mask portion 13 includes a mount member 15 molded from a relatively stiff plastics material, such as PVC. The mount member 15 has a hollow cylindrical sleeve 17 at its rear end, in which the forward, patient end 14 of the tube 1 is inserted and joined. The forward, patient end 18 of the mount member 15 is of an inverted dish shape with a generally elliptical or egg-shaped outline and with a concave recess 19. A bore 20 extends forwardly through the mount member 15, as a continuation of the bore through the sleeve 17, and opens into the rear part of the recess 19. The forward surface of the mount member 15 has a projection 21 of inverted V-shape at its forward tip, the purpose of which will become apparent later. The rear surface of the mount member 15 has an upwardly-projecting lip 22 extending around the major part of its periphery and, within the lip, a recessed channel 23.

The mask portion 13 also includes an inflatable cuff 30 attached around the edge of the mount member 15. The cuff 30 is extruded from a flexible, resilient plastics material, such as PVC, polyurethane, silicone, EVA, TPE, polyether block amide or the like. The main part of the cuff 30 is provided by a tubular portion 31 of circular section. The cuff 30 also has an integral flange or attachment member 32 projecting laterally outwardly from the tubular portion 31 along, its length. The outer end of the flange 32 has a downwardly-projecting tooth 33, which defines a channel 34 along the underside of the flange, between the tubular portion 31 and an inner edge of the tooth. The cuff 30 could be made by other techniques such as pulsed (bubble) extrusion or blow molding, or by a combination of extrusion and subsequent blow molding to produce regions of reduced wall thickness and different diameters. The cuff 30 is folded around the outer edge of the mount member 15, with its flange 32 projecting inwardly and overlapping the outer edge of the mount member. In particular, the tooth 33 on the flange 32 locates in the channel 23 in the mount member 15, and the lip 22 on the mount member locates in the channel 34 on the flange. Opposite ends of the cuff 30 are fitted over two spigots 35 protruding from opposite arms the projection 21 on the mount member 15. A solvent, adhesive or heat bond is used to join the contacting surfaces of the cuff 30 and mount member 15 to one another.

The cuff 30 can be inflated and deflated in various different ways. For example, the projection 21 and spigots 35 could be hollow and communicate with the inflation lumen 2 via a gas passage formed in the mount member 15, so that gas can be supplied to or from opposite ends of the cuff 30. Alternatively, a separate small-bore tube could be connected between the inflation lumen and the interior of the cuff.

The cuff could have various different sections, thus controlling the shape of the cuff when deflated by the application of a vacuum, for insertion into the patient. For example, as shown in FIG. 4, the cuff 30' has a flange 32' of arrow-head shape with two oppositely-projecting teeth 33'. This flange 32' can be a snap fit into a recess (not shown) in the mount member of a corresponding shape. The ends of the cuff need not be joined at the tip of the mount member but could instead be joined at the opposite end or heel.

The cuff could be filled with a foam to make it self-inflating and negative pressure applied via the lumen 2 to suck down the cuff for insertion and removal.

What I claim is:

1. A laryngeal mask assembly comprising: an elongate tube and a mask portion at the patient end of the tube, wherein said mask portion includes a mount member of generally elliptical shape, said mount member having an opening therethrough communicating with a patient end of said tube, where said mask portion includes a hollow elongate cylindrical cuff member having a first end and a second end opposite said first end, said cuff member having an attachment flange projecting laterally of the cuff member along its length extending between said ends, and wherein said cuff member is attached with said mount member by bending said cuff member along the edge of said mount member, attaching said flange with said mount member, and by sealing said opposite ends of said cuff member at a location on said mount member.

2. A laryngeal mask assembly according to claim 1, wherein said mount member has two spigots, and wherein said opposite ends of said cuff member are sealed to respective ones of said spigots.

3. A laryngeal mask assembly according to claim 2, wherein said tube has an inflation lumen extending along its length, and wherein at least one of said spigots communicates with said inflation lumen so that said cuff member can be inflated via said lumen and a spigot.

4. A laryngeal mask assembly according to claim 1, wherein said attachment flange has a projecting member extending along its length, and wherein said projecting member defines a channel between said projecting member and a tubular portion of said cuff member.

5. A laryngeal mask assembly according to claim 4, wherein said mount member has a channel extending around its outer edge, and wherein said projecting member on said attachment flange is located in the said channel on said mount member.

6. A laryngeal mask assembly according to claim 1, wherein the said attachment flange is of arrow shape cross-section.

7. A laryngeal mask assembly comprising: an elongate tube and a mask portion at the patient end of the tube, wherein said mask portion includes a mount member of generally elliptical shape, with a forward surface and a rear surface, said mount member having an opening therethrough communicating with a patient end of said tube, said mount member having a channel extending around said rear surface, wherein said mask portion includes a hollow cylindrical cuff member having a first end and a second end opposite said first end, said cuff member having an attachment flange projecting laterally of the cuff member along its length, and said flange having a tooth member projecting therefrom, and wherein said cuff member is attached with said mount member by bending the cuff member along its length around said mount member, locating said tooth member in said channel and sealing said opposite ends of said cuff at a location on said mount member.

8. A method of manufacture of a laryngeal mask assembly comprising the steps of: providing an elongate tube, said tube having a mount member at its patient end, said mount member being of generally elliptical shape and having an opening therethrough communicating with a patient end of said tube; providing a hollow cylindrical cuff member having a first and a second end opposite said front end, said cuff member having an attachment flange projecting laterally along its length between said ends; folding said cuff member along its length about an outer edge of said mount member; attaching said attachment flange to said mount member and sealing said opposite ends of said cuff member at a location on the mount member.

9. A method according to claim 8, wherein said cuff member is extruded.

\* \* \* \* \*